(12) United States Patent
    Wiese

(10) Patent No.: US 9,056,895 B1
(45) Date of Patent: Jun. 16, 2015

(54) METHODS OF ISOLATING PEPTIDES USING SURFACE-FREE AFFINITY PURIFICATION

(71) Applicant: WELLSPRING CLINICAL LAB, INC., Altamonte Springs, FL (US)

(72) Inventor: Calvin Wiese, Altamonte Springs, FL (US)

(73) Assignee: WELLSPRING CLINICAL LAB, INC., Altamonte Springs, FL (US)

( * ) Notice: Subject to any disclaimer, the term of this patent is extended or adjusted under 35 U.S.C. 154(b) by 0 days.

(21) Appl. No.: 13/886,978

(22) Filed: May 3, 2013

Related U.S. Application Data

(62) Division of application No. 13/253,619, filed on Oct. 5, 2011, now Pat. No. 8,450,465.

(60) Provisional application No. 61/390,485, filed on Oct. 6, 2010.

(51) Int. Cl.
| | |
|---|---|
| *G01N 30/02* | (2006.01) |
| *C07K 1/22* | (2006.01) |
| *C07K 1/20* | (2006.01) |
| *C07K 1/36* | (2006.01) |
| *G01N 30/00* | (2006.01) |
| *G01N 33/566* | (2006.01) |

(52) U.S. Cl.
    CPC ... *C07K 1/22* (2013.01); *C07K 1/20* (2013.01); *G01N 30/02* (2013.01); *C07K 1/36* (2013.01); *G01N 30/00* (2013.01); *G01N 33/566* (2013.01)

(58) Field of Classification Search
    CPC .............. C07K 1/20; C07K 1/22; C07K 1/36; G01N 30/00; G01N 30/02; G01N 33/566
    See application file for complete search history.

(56) References Cited

U.S. PATENT DOCUMENTS 6,812,023 B1   11/2004   Lamparski et al.

OTHER PUBLICATIONS

Porter J, et al. Absolute Quantification of the Lower Abundance Proteome Through Immunoaffinity Depletion of the Twenty Most Abundant Proteins in Human Serum. Sigma-Aldrich Biotechnology. Retrieved from the internet Jun. 16, 2014.*
Qian W-J, et al. Molecular & Cellular Proteomics. 7:1963-1973, 2008.*
Lev, et al., Cancer Research, 2002, 62:3184-3194.
Lyubarskaya, et al., Anal Chem., 1997, 69, 3008-3014.

* cited by examiner

*Primary Examiner* — Robert Landsman
(74) *Attorney, Agent, or Firm* — Drinker Biddle & Reath LLP

(57) ABSTRACT

The present invention, referred to as Surface-Free Affinity Purification (SFAP), relates to a system and method for purifying low abundance peptides, including digested plasma proteins. SFAP combines the components and processes of Surface-Free Isolation, Specific Competitive Elution, Dual Epitope Isolation and Protective Solvents in the purification of low abundance proteins, all of which may be performed in a single column. This column is a constant volume Diafiltration Column equipped with stirring that can be driven by an HPLC. Digested plasma may be injected into the Diafiltration Column by the HPLC. Immunoglobulins, Specific Competitive Elutants, Protective Solvents are injected in a series of injections that result in the purified peptides bound to the surfaces of a very-low volume hydrophobic reversed phase trap from which they can be easily injected into mass spectrometry detection instruments.

19 Claims, 3 Drawing Sheets

METHODS OF ISOLATING PEPTIDES USING SURFACE-FREE AFFINITY PURIFICATION

CROSS-REFERENCE TO RELATED PATENT APPLICATIONS

This patent application is a divisional of U.S. patent application Ser. No. 13/253,619, filed Oct. 5, 2011 and now issued U.S. Pat. No. 8,450,465, which claims the benefit of U.S. Provisional Patent Application No. 61/390,485 filed Oct. 6, 2010, both of which are herein incorporated by reference.

FIELD OF THE INVENTION

This invention pertains to systems and methods of protein purification, and more particularly to the purification of low-abundance peptides from high complexity, high dynamic range protein digests such as plasma, including a column for isolating tryptic peptides and other small molecules from immunoglobulins and other large affinity molecules.

BACKGROUND OF THE INVENTION

The complexity of the plasma proteome is extraordinary, and unlocking its secrets is considered one of the great challenges of modern day science. There is broad scientific belief that the plasma proteome is made up of many thousands of proteins, only about 2,000 of which have been detected. Of the detected proteins, the most abundant is albumin, which accounts for about one half of all plasma proteins. The top twenty most abundant proteins account for around ninety nine percent of all plasma proteins, while the remaining thousands of plasma proteins are in low-abundance, and amount to only about one percent of all the plasma proteins in total. An example of this vast dynamic range is the protein interleukin-6; for each interleukin-6 protein there are about ten billion albumin proteins. As such, it is extremely challenging to detect and measure proteins as low in abundance as interleukin-6.

Immunoglobulins are equipped with affinity receptors that are capable of capturing low abundance proteins in spite of the high complexity of the proteome. Affinity receptors capture molecules on the basis of their affinity; unfortunately, affinity is not binary—affinity is continuous. Accordingly, affinity receptors are not specific. As such, while targeted low abundance proteins are captured by affinity receptors, many other proteins get captured with them. Instead of purifying the targets, affinity receptors merely enrich their targets.

Beyond affinity receptor lack of specificity, isolation platforms utilized for affinity receptors are highly susceptible to non-specific binding of high abundant proteins through their near-universal use of surfaces. Most proteins have surfaces with hydrophobic and static electric charge characteristics that tend to make them "sticky" to other surface types. Nearly all isolation platforms use surfaces that attract high quantities of high abundance sticky proteins.

Sticky surfaces and unspecific affinity receptors create very high barriers to purification. Without ready purification capability, low abundance proteins continue to hide deep down in the largely unexplored depths of the plasma proteome.

Mass spectrometry is, perhaps, the most powerful detection platform for proteins. Its high specificity detection capabilities are universal for nearly any protein. But, because of mass spectrometry's need for enrichment or purification, these significant detection capabilities are largely unused for exploring the depths of the plasma proteome. Lacking sufficiently effective enrichment or purification methods, this powerful detection tool is not widely used to explore the depths of the plasma proteome.

Therefore, there is a strong need for a protein purification device, system and method for isolating low-abundance peptides, such as those found within the plasma proteome. The present invention satisfies this need.

BRIEF DESCRIPTION OF THE DRAWINGS

In order to aid in understanding the invention, it will now be described in connection with exemplary embodiments thereof with reference to the accompanying drawings in which like numerical designations will be given to like features with reference to the accompanying drawings wherein.

DETAILED DESCRIPTION OF THE INVENTION

Figure 1:
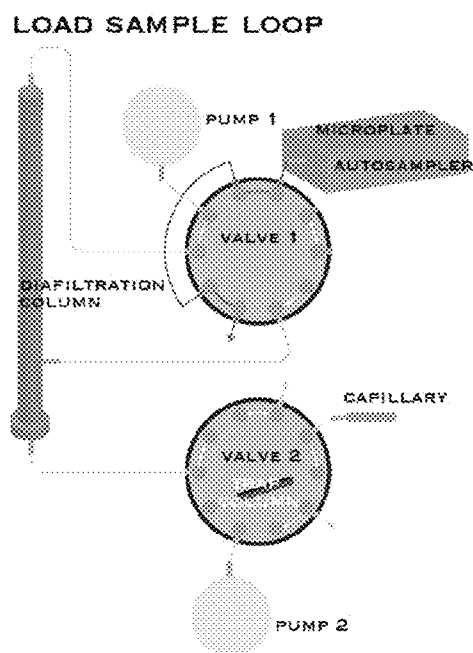
FIG. 1 illustrates a Load Sample Loop state. This state loads the sample loop with samples and reagents injected by an autosampler.

The various embodiments of the invention described in detail below are not intended to be exhaustive or to limit the invention to any particular structure and/or operation disclosed. Rather, the described embodiments have been chosen and described to explain the principles of the invention and its application, operation and use in order to best enable others skilled in the art to follow its teachings.

The present invention, also referred to herein as Surface-Free Affinity Purification (SFAP), is a simple, inexpensive and robust method for purifying low abundance peptides, including digested plasma proteins. SFAP combines the components and processes of Surface-Free Isolation, Specific Competitive Elution, Dual Epitope Isolation and Protective Solvents in the purification of low abundance proteins, all of which may be performed in a single column. This column is a constant volume Diafiltration Column equipped with stirring that can be driven by an HPLC. Digested plasma may be injected into the Diafiltration Column by the HPLC. Immunoglobulins, Specific Competitive Elutants, Protective Solvents are injected in a series of injections that result in the purified peptides bound to the surfaces of a very-low volume hydrophobic reversed phase trap from which they can be easily injected into mass spectrometry detection instruments. In one exemplary embodiment, SFAP is directed to peptide digests, where larger proteins and/or complexes are cleaved into variable length peptides, and the targeted peptides are purified. Immunoglobulins are used in SFAP as affinity receptors. In alternative embodiments, other types of receptor molecules, such as aptamers, may also be used in SFAP.

For example, Surface-Free Isolation exploits the wide size/mass differences of peptide digests from immunoglobulins to isolate immuno-complexes. By exploiting this difference, it can avoid the surfaces typically associated with immuno-complex isolation methods. Because the surfaces are "sticky" to the high abundance non-specific peptides, eliminating the surfaces avoids a great amount of non-specific bindings.

Further, Specific Competitive Elution is a method to elute target peptides from their binding receptors while maintaining physiological conditions. Specific Competitive Elution peptides are synthesized peptides with amino acid sequences specific to the receptor binding epitope. They are labeled with tails that facilitate the downstream separation from target peptides. Specific Competitive Elution peptides compete for binding sites with the target bound peptides. Excess amounts of Specific Competitive Elution peptides overload binding receptors forcing the target peptides out.

Typical elution methods create conditions where fragile receptors such as immunoglobulin proteins are slightly deformed to break/release the binding. Usually, these conditions also result in releasing any other sticky proteins that might be sticking to the immunoglobulin surfaces other than the receptor binding surfaces. With Specific Competitive Elution, only the specific peptides bound to the receptors are eluted.

A further benefit of Specific Competitive Elution is that the conditions are retained in which subsequent bindings can be undertaken. This benefit is exploited for Dual Epitope Isolation. Dual Epitope Isolation deals with the lack of specificity of the affinity receptors. The peptides captured by the first receptor include the target peptide along with peptides with lower affinity to the receptor. The second receptor captures peptides from the population of peptides eluted from the first receptor capture. As such, only those peptides with both orthogonal epitopes are captured.

This orthogonal selectivity is similar to the well-developed "sandwich" immunoassay. Sandwich immunoassays use two immunoglobulins directed at two different epitopes; the first immunoglobulin isolates, the second immunoglobulin reports the proteins that bind orthogonally to both epitopes.

As mentioned previously, Protective Solvents are employed to protect the high purity, low abundance target peptides from surface adsorption losses. When high-purity, low-abundance, electrically charged, hydrophobic peptides that are unbound and moving freely encounter surfaces, large proportions of them will adsorb onto those surfaces. When the solution is largely free of other molecules that would otherwise had been attracted to these surfaces, the only peptides available to these surfaces are the very few purified target peptides. Protective Solvents are solvents carrying abundant molecules with 1) propensity to adsorb onto surfaces and 2) naturally occurring labels for downstream separations from targets.

The Diafiltration Column consists of a column having three ports, including: 1) an input port through which solution is injected into the Diafiltration Column; 2) an output port which is obstructed by a membrane capable of retaining the receptor molecule while allowing the ligand molecule to pass through; and 3) a vent port which is obstructed by a membrane capable of retaining the ligand molecule. The output port is used for solution to exit the Diafiltration Column when the solution is being exchanged, or washed out. The vent port is used for solution to exit the Diafiltration Column when samples and reagents are being injected. An alternative embodiment combines the output port and the exit port by providing a mechanism to switch membranes. In a further alternative embodiment, the vent port may be eliminated. It should be appreciated that alternative platforms beyond the HPLC platform exist for implementing the Diafiltration Column as contemplated herein. For example, these may include microfluidic platforms that combine several of the required components into a unified complex component.

Figure 2:
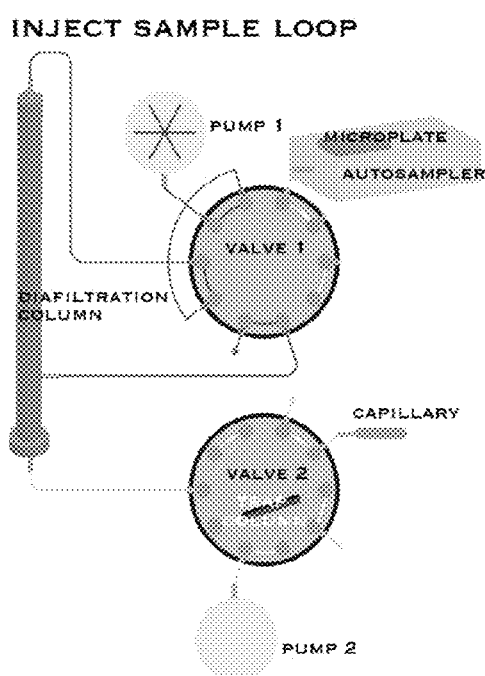
FIG. 2 illustrates an Inject Sample Loop state. This state injects the solution in the sample loop into a Diafiltration Column. While in this state, the output port is blocked and the vent port is directed to waste.
Figure 3:
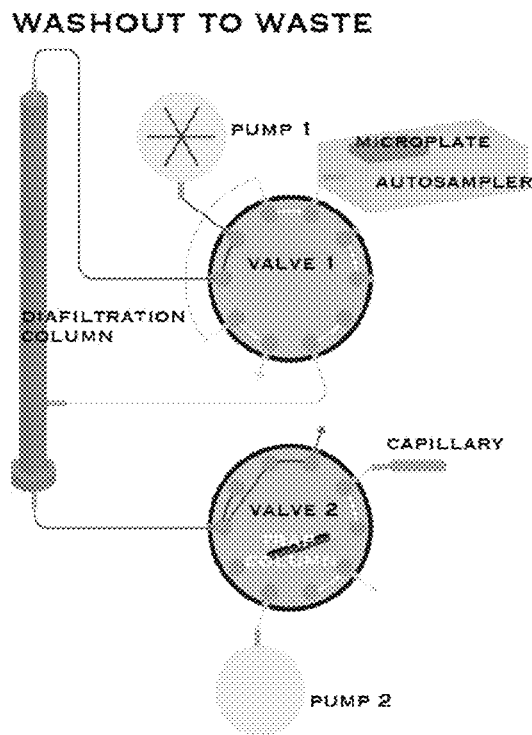
FIG. 3 illustrates a Washout to Waste state. This state pumps solution through the Diafiltration Column and exits through the output port. While in this state, the output port is directed to waste and the vent port is blocked.
Figure 4:
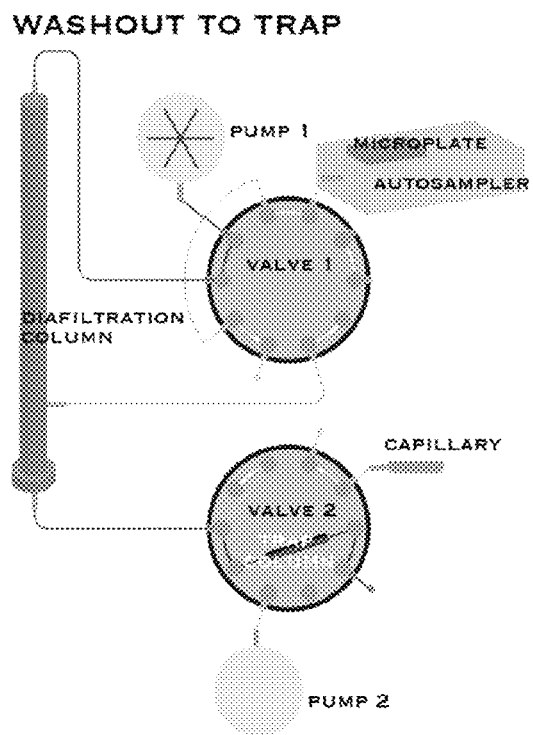
FIG. 4 illustrates a Washout to Trap state. This state pumps solution through the Diafiltration Column and exits through the output port into the Trap Column. While in this state, the output port is directed to the Trap Column input port, the Trap Column output port is direct to waste and the vent port is blocked.
Figure 5:
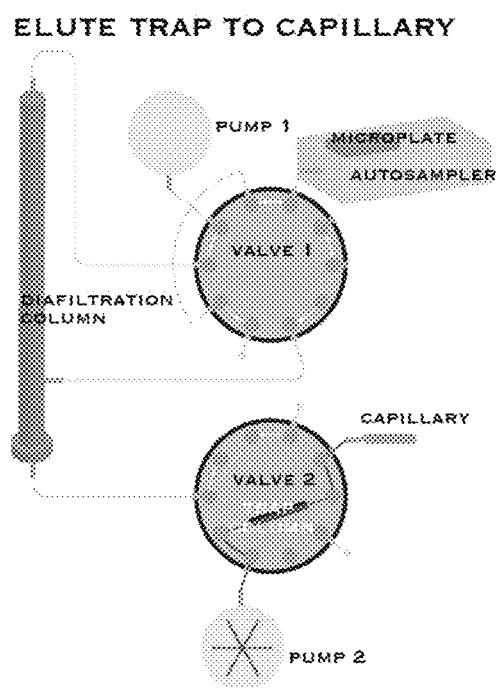
FIG. 5 illustrates an Elute Trap to Capillary state. This state pumps solution through the Trap Column and exits into a capillary tube. While in this state, the Trap Column output port is directed to the capillary input and the capillary output is directed to waste.

As contemplated herein, FIGS. 1-5 illustrate an exemplary HPLC setup for each of the various states required for performing each step in the Surface-Free Affinity Purification process. Central to each of FIGS. 1-5 is a Diafiltration Column, in which each of the steps identified therein are performed. The Diafiltration Column is supported by standard HPLC equipment as would be understood by those skilled in the art, including two solvent pumps, two 10 position rotary valves, one autosampler and one reversed-phase Trap Column. Illustrated in FIG. 1 is a Load Sample Loop state. This state loads the sample loop with samples and reagents injected by an autosampler. Illustrated in FIG. 2 is an Inject Sample Loop state. This state injects the solution in the sample loop into a Diafiltration Column. While in this state, the output port is blocked and the vent port is directed to waste. Illustrated in FIG. 3 is a Washout to Waste state. This state pumps solution through the Diafiltration Column and exits through the output port. While in this state, the output port is directed to waste and the vent port is blocked. Illustrated in FIG. 4 is a Washout to Trap state. This state pumps solution through the Diafiltration Column and exits through the output port into the Trap Column. While in this state, the output port is directed to the Trap Column input port, the Trap Column output port is direct to waste and the vent port is blocked. Illustrated in FIG. 5 is an Elute Trap to Capillary state. This state pumps solution through the Trap Column and exits into a capillary tube. While in this state, the Trap Column output port is directed to the capillary input and the capillary output is directed to waste.

The present invention includes a method of isolating affinity complexes from peptide digests. The method may comprise the steps of capturing target peptides using affinity molecules that are substantially larger than the target peptides, most preferably, greater than 30 kDa, and separating the affinity complex from the peptide digest using any means of separating molecules that is based on either the size of the molecule or the mass of the molecule.

The present invention also includes a method of eluting target ligand molecules from receptor molecules. The method may comprise the steps of adding excess amounts of labeled ligand molecules to compete with and drive off the bound target ligand molecules from receptor sites, and separating the target ligand molecules from the labeled ligand molecules on the basis of the label.

The present invention also includes a method of protecting high purity, low abundance molecules from adsorption onto surrounding surfaces. The method may comprise the steps of providing solvents carrying labeled molecules that have a propensity to adsorb to surrounding surfaces, and are labeled such that they can be easily separated from the high purity, low abundance molecules through downstream separation processes.

The present invention further includes a method of purifying target molecules from complex solutions where receptor molecules size or mass substantially exceeds the size or mass of the target molecule, as well as the size or mass of the non-target molecules in the complex solution. The method comprises the steps of: a) isolating target molecules through affinity capture with a first receptor molecule; b) separating resulting affinity complex from complex solution on the basis of either size or mass; c) eluting target molecules from the first receptor molecules using specific competitive elution molecules specific to the first receptor molecule; d) further isolating target molecules through affinity capture with a second receptor molecule; e) separating resulting affinity complex from solution on the basis of either size or mass; f) eluting target molecules from the second receptor molecules using specific competitive elution molecules specific to the second receptor molecule; and g) separating the target molecules from the specific competitive elution molecules on the basis of the specific competitive elution molecule label.

The present invention further includes a method of purifying target molecules from complex solutions where receptor molecules size or mass substantially exceeds the size or mass of the target molecule, as well as the size or mass of the non-target molecules in the complex solution. The method comprises the steps of: a) isolating target molecules through affinity capture with a receptor molecule; b) separating resulting affinity complex from complex solution on the basis of either size or mass; c) eluting target molecules from the receptor molecules using specific competitive elution molecules specific to the first receptor molecule; and d) separating the target molecules from the specific competitive elution molecules on the basis of the specific competitive elution molecule label.

The present invention also includes a method of purifying target molecules from complex solutions comprising the steps of: a) isolating target molecules through affinity capture with a first receptor molecule; b) separating resulting affinity complex from complex solution through receptor molecule immobilization; c) eluting target molecules from the first receptor molecules using specific competitive elution molecules specific to the first receptor molecule; d) further isolating target molecules through affinity capture with a second receptor molecule; e) separating resulting affinity complex from solution through receptor molecule isolation; f) eluting target molecules from the second receptor molecules using specific competitive elution molecules specific to the second receptor molecule; and g) separating the target molecules from the specific competitive elution molecules on the basis of the specific competitive elution molecule label.

Surface-Free Isolation

The formation of immuno-complexes between immunoglobulins and peptide digests for the purpose of isolating target peptides is becoming increasingly important as increasing volumes of peptide targeted immunoglobulin content is being developed. To a large extent, this content is being implemented on the isolation platforms historically developed for isolating immuno-complexes targeting intact proteins. While typical intact protein matrices exhibit very large mass distributions that largely overlap the masses of immunoglobulins, the peptide digest mass distribution is very narrow and much smaller than the masses of immunoglobulins. This characteristic presents the opportunity to exploit these significant mass differences for isolation of immuno-complexes in a way that eliminates many issues associated with the typical isolation platforms.

The masses of tryptic peptides are in the range of about 1,000 to 3,000 Daltons. The mass of immunoglobulins is about 150,000 Daltons, which is approximately 50 to 150 times that of tryptic peptides. The present invention exploits this significant mass difference as a "label" for isolation purposes.

Virtually all isolation platforms exploit some form of label. Typically, that label must be exogenously attached. Probably the most typical form of immunoglobulin labeling is immobilization, which is usually to a surface. Labeling, in general, and isolation, specifically, gives rise to costs in the form of lower efficiencies and more steps. In most cases, the lower efficiencies can be dramatic. For example, immobilizing immunoglobulins results in lower biological activity (nearly every step in the immobilization process has some denaturing affect) and, very significant reduction in mobility. Since diffusion is critical in capture reactions, the dramatic reductions in mobility that accompany immobilization can significantly diminish the efficiency and effectiveness of the capture reactions—a high price paid in most immuno-complex processes.

By exploiting the naturally-occurring label of the significant mass difference between the peptides and the immuno-complexes formed in accordance with the present invention, much more efficient capture reactions can be realized than has heretofore been the case. Further, the present invention requires fewer immunoglobulins, along with lower cost to prepare immunoglobulins for capture.

When surfaces are employed for immobilizing immunoglobulins (which includes almost every case including the two phase captures that do the initial capture in liquid and then capture the immuno-complexes on a surface), the surfaces attract non-specific molecules. In many cases, these surface areas are massive in comparison with the surface area of the immunoglobulin. By avoiding these surfaces, the non-specific binding to surface area is eliminated. Since a major portion of the non-specific binding associated with plasma tryptic peptide digests are related to bindings to surfaces, eliminating the surface significantly reduces non-specific bindings.

Isolating immuno-complexes from peptide digests on the basis of size or mass is a low degree of difficulty separation problem. Several separation methods are very capable of solving this problem. Such methods include, but are not limited to, 1) ultracentrifugation, 2) field flow fractionation, 3) size exclusion chromatography, 4) gel permeation chromatography, 5) ultra-filtration, 6) diafiltration, 7) dialysis and 8) electrophoresis.

The ultracentrifugation method employs centrifugal force to sediment the immuno-complexes through a column that isolates immuno-complexes from peptide digest. Centrifugal force is a force proportionate to mass. As such it exploits the wide differences in mass and corresponding sedimentation velocity to effect the separation of the immuno-complex from the peptide digest into zones of the column. Since the sedimentation coefficients of peptides is in the range of about 0.7 Svedberg and the sedimentation coefficients for immunoglobulins are in the range of about 7 Svedberg, there is about a 10-fold difference in sedimentation velocity between peptides and immuno-complexes. As such, the immuno-complexes easily separate from the peptides.

The field flow fractionation method entails the application of one or more of gravitation, centrifugal, magnetic, thermal, or a cross flow of fluid field forces in which the field forces the mixtures of the tryptic peptides and the immunoglobulins onto one side. The balance between diffusion and the applied force from the field on the tryptic peptides and the immunoglobulins results in differing movement vertically to separate the two components. When the field is turned on, the tryptic peptides and the immunoglobulins will be exposed to a velocity profile such that the tryptic peptides at a higher height from the base will travel faster than the immunoglobulins at the bottom, thus producing the desired separation.

The size exclusion chromatography and similarly with the gel permeation chromatography methods employ the underlying principle that particles of different sizes will elute (filter) through a stationary phase at different rates. This results in the separation of a solution of particles based on size.

Provided that all the particles are loaded simultaneously or near simultaneously, particles of the same size elute together; thus, the immunoglobulins will elute first, then the peptides will elute producing the desired separation.

The ultra-filtration method would flow the sample through an ultra-filtration membrane with a pore size such that the immunoglobulins will be retained by the membrane while the peptides will pass through the membrane producing the desired separation.

The diafiltration method flows the sample through an ultra-filtration membrane with a pore size such that the immunoglobulins will be retained by the membrane while the peptides will pass through the membrane producing the desired separation. As the sample flows through the membrane, the sample is replaced with solvent such that the sample volume remains fixed and constant.

The electrophoresis method separates the molecules on the basis of the mass/charge ratios. Since the mass of the immunoglobulins is very high compared to the peptides, while the charges are similar, the mass/charge ratio is much higher for immunoglobulins; accordingly electrophoresis can be employed to produce the desired separation.

Dual Epitope Isolation

Affinity receptors bind molecules that possess some affinity to the receptor. Different molecules have different levels of affinity for receptors; high affinity molecules bind tightly to its receptor, lower affinity molecules bind less tightly. As such, affinity receptors are not highly specific in that they can bind to a variety of molecules with various affinities.

The specificity of immunoglobulins to peptides is not sufficiently high to achieve high levels of purification of low abundance plasma peptides. But, by orthogonally deploying dual immunoglobulins that bind at dual epitopes, high specificity can be achieved.

Dual epitopes, orthogonally deployed, are routinely employed by the "sandwich" immunoassay. In the "sandwich" immunoassay, the first immunoglobulin is used to isolate molecules with sufficient affinity. Then, the second immunoglobulin, directed toward the second epitope, is used as a detector of the molecules that match both orthogonal epitopes achieving high specificity detection.

While traditionally deployed by the "sandwich" immunoassay, dual epitopes have been rarely utilized in analytical peptide isolation methods. In order to deploy dual epitopes for isolation, there must be a release of the first epitope so that the second epitope can isolate the matching molecules from the population of molecules that were bound by the first epitope. To release molecules, eluting conditions are required in which immunoglobulins are deformed in order to break the binding and release the ligand. Those conditions, once present, are not the conditions required for the subsequent epitope binding. Accordingly, the conditions would have to be restored in order to achieve subsequent epitope binding. This need to restore binding conditions is avoided by the use of specific competitive elutants.

Specific Competitive Elution

Specific Competitive Elution employs peptides with amino acid sequences specific to the epitope to competitively drive off the bound peptides. Typically, elution is accomplished through modifying the solvent to conditions in which the antibody is disformed sufficiently to break the bindings, typically through either a change in pH, or increasing organic content. Specific Competitive Elution avoids the need to change solvent conditions; solvent remains at physiological conditions so that the antibody is not disformed. Disformation of antibodies typically drive off any non-specific antibodies that might be adsorbed to the antibody surface. Maintenance of physiological conditions facilitates multiple serial epitope isolations.

Specific Competitive Elution contaminates the target peptides they drive off. Accordingly, in order to purify the target peptides, there needs to be a subsequent separation of the Specific Competitive Elution peptides from the target peptides. This subsequent separation can be easily and cleanly accomplished through appropriate labeling of the Specific Competitive Elution peptides. Since the Specific Competitive Elution peptides are synthesized, they can be designed with a variety of label forms to suit whatever is optimal for the downstream separation method.

An attractive label form is hydrophilicity. This can work well when the downstream separation method is a hydrophobic trap. The hydrophobic trap will typically use reversed phase media that will bind the relatively hydrophobic target peptides. Hydrophilic Specific Competitive Elution peptides will flow through the trap, separating them from the target peptides that are trapped on the reversed phase media.

Another label form is fluorous. Fluorous labeling can be ultra-hydrophobic. This can work when the downstream separation method is a hydrophobic trap. The hydrophobic trap will typically use reversed phase media that will bind the relatively hydrophobic target peptides. Fluorous Specific Competitive Elution peptides will bind strongly to the trap along with the target peptides. Separation is achieved through elution. While the target peptides will typically elute with a mild organic (<40% acetonitrile) the fluorous labeled Specific Competitive Elution peptides can be designed to require a strong organic elutant or even a fluorous elutant.

Protective Solvents

Purifying very low abundance peptides results in very few peptides dissolved in lots of liquid. In such conditions, the hydrophobic peptides face high peril of adsorption to surfaces and high percentages of these precious few peptides are typically lost. In more typical conditions of low purity, there are multitudes of other molecules that compete for the surface attraction sites such that the targets are largely protected from these adsorption perils.

Protective Solvents are employed to protect the high purity, low abundance target peptides from surface adsorption losses. Protective Solvents are solvents carrying abundant molecules with 1) propensity to adsorb onto surfaces and 2) labels for downstream separations from targets. Surface-Free Affinity Purification utilizes two solvent forms; 1) aqueous and 2) organic.

The aqueous solvent is used for diafiltration washout; essentially exchanging the sample solvent. As such, it is formulated to maintain physiological conditions and is typically some variant of phosphate buffered saline (PBS). The protective molecules that it carries will typically be biological molecules that are electrically charged and hydrophilic. The electrical charge will typically predispose the molecule to surface adsorption. The hydrophilicity serves as a natural label for separation from the target hydrophobic peptides that are trapped on the reversed phase trap; the protective molecules flow through the trap due to their hydrophilicity while the target peptides bind to the traps hydrophobic functional groups. Some form of hydrophilic amino acid such as arginine and lysine are possible aqueous protective molecules.

The organic solvent is used to elute the trapped hydrophobic target peptides from the reversed phase trap. As such, the solvent is more hydrophobic then the reversed phase functional groups such that the hydrophobic peptides desorb from the reversed phase functional groups into the solvent. The solvent carries the target peptides to the mass spectrometry interface. As such, the molecules carried by the organic solvent are subject to mass spectrometry ionization conditions. The ideal protective molecules in the organic solvent will 1) adsorb to surfaces and 2) be difficult to ionize. Separation of the protective molecules from the target peptides occurs at ionization; hence a natural label of the protective molecules is their low ionization efficiency. Some form of lipid like cholesterol has the potential to be an ideal organic protective molecule.

Diafiltration Column

Surface-Free Affinity Purification may be performed in a constant-volume Diafiltration Column where liquid flows through a membrane to purify the retained molecules without concentrating them. Concentration is avoided by the "constant-volume" characteristics; equal amounts of liquid are replaced as liquid flows through the membrane. The membrane pore size is sufficiently small to retain immuno-complexes while peptides flow through.

An important feature of such a Diafiltration Column is stirring. As liquid flows through the membrane, the retained molecules are concentrated on the membrane surface. Stirring is important to disrupt this concentration and provide counter-current forces to distribute the concentrating molecules away from the surface. Any stirring mechanism may be used, including mechanical vibration, rotational stirring via a magnetic stirring bar or a blender blade, or any other mechanism suitable for stirring as would be understood by those skilled in the art.

The Diafiltration Column is a chamber with ports. The chamber holds the constant-volume sample and facilitates it's stirring. Input and output ports are required. A single input port facilitates the injection of sample and reagents as well as the wash-out solvent. The output port is obstructed by the membrane with pore sizes such that the target peptides flow through and the immunoglobulin receptors are retained to facilitate the wash-out process. Another output port that retains target peptides and flows through solvent may be provided to facilitate injection of sample and reagents. Alternatively, a single output port with a changeable membrane may accommodate both wash-out and injection processes.

Example Purification Processes

According to another aspect of the present invention, there are various ways in which the components of Surface-Free Affinity Purification can be arranged to perform purification. For example, in Dual Epitope Peptide Purification, the following steps may be performed: 1) Inject plasma peptide digest. In this step, the Diafiltration Column states used are Load Sample Loop and Inject Sample Loop; 2) Inject mass-shifted isotopic internal standards. In this step, the Diafiltration Column states used are Load Sample Loop and Inject Sample Loop; 3) Inject first epitope antibodies. In this step, the Diafiltration Column states used are Load Sample Loop and Inject Sample Loop; 4) Incubate to equilibrium; 5) Washout to waste. In this step, the Diafiltration Column state used is Washout to Waste; 6) Inject second epitope antibodies. In this step, the Diafiltration Column states used are Load Sample Loop and Inject Sample Loop; 7) Inject first epitope specific competitive elutants. In this step, the Diafiltration Column states used are Load Sample Loop and Inject Sample Loop; 8) Incubate to equilibrium; 9) Washout to waste. In this step, the Diafiltration Column state used is Washout to Waste; 10) Inject second epitope specific competitive elutants. In this step, the Diafiltration Column states used are Load Sample Loop and Inject Sample Loop; 11) Incubate to equilibrium; 12) Washout to trap. In this step, the Diafiltration Column state used is Washout to Trap; and 13) Elute trap to capillary. In this step, the Diafiltration Column state used is Elute Trap to Capillary.

Another way in which the components of Surface-Free Affinity Purification can be arranged to perform purification is Single Epitope Peptide Purification. In this process, the following steps may be performed: 1) Inject plasma peptide digest. In this step, the Diafiltration Column states used are Load Sample Loop and Inject Sample Loop; 2) Inject mass-shifted isotopic internal standards. In this step, the Diafiltration Column states used are Load Sample Loop and Inject Sample Loop; 3) Inject antibodies. In this step, the Diafiltration Column states used are Load Sample Loop and Inject Sample Loop; 4) Incubate to equilibrium; 5) Washout to waste. In this step, the Diafiltration Column state used is Washout to Waste; 6) Inject specific competitive elutants. In this step, the Diafiltration Column states used are Load Sample Loop and Inject Sample Loop; 7) Incubate to equilibrium; 8) Washout to trap. In this step, the Diafiltration Column state used is Washout to Trap; and 9) Elute trap to capillary. In this step, the Diafiltration Column state used is Elute Trap to Capillary.

According to another aspect of the present invention, Surface-Free Affinity Purification can also be used to purify metabolites and other molecules beyond just peptides. The primary constraint is availability of a receptor molecule that is substantially larger than the target molecule. For example, the present invention may be used for Vitamin D with Vitamin D Receptor Protein, Estrogen with Sex Hormone Binding Globulin, Testosterone with Sex Hormone Binding Globulin, and Vitamin B12 with Vitamin B12 Aptamer.

Isotopes of target molecules can be employed as Specific Competitive Elutants, particularly when mass spectrometry is used for detection. In such cases, assays may require two different isotopes of the target molecule; one for internal standard quantification and the other for Specific Competitive Elutant.

Dual Epitope Isolation can also be performed without Surface-Free Isolation using well known immobilization techniques for isolation along with Specific Competitive Elutants and Protective Solvents. An example workflow for using Dual Epitope Isolation that employs magnetic beads for isolation may include the following steps of: 1) Aspirate plasma peptide digest; 2) Aspirate mass-shifted isotopic internal standards; 3) Aspirate first epitope biotinylated antibodies; 4) Incubate to equilibrium; 5) Aspirate streptavidin magnetic beads; 6) Incubate to equilibrium; 7) Remove magnetic beads and wash in protective solvent; 8) Aspirate second epitope antibodies; 9) Aspirate first epitope specific competitive elutants; 10) Incubate to equilibrium; 11) Remove magnetic beads; 12) Aspirate second epitope specific competitive elutants; 13) Incubate to equilibrium; 14) Aspirate protein G magnetic beads; 15) Incubate to equilibrium; 16) Remove magnetic beads; 17) Aspirate solution into reversed phase pipette tip and wash pipette tip; and 18) Elute reversed phase pipette tip with organic protective solvent onto laser desorption plate.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

I claim:

1. A method of eluting target ligand molecules bound to receptor molecules comprising:
   providing a sample solution containing target peptide ligand molecules bound to receptor molecules in the absence of immobilizing surfaces, where the receptor molecules are substantially larger than the target peptide ligand molecules;
   adding excess amounts of labeled ligand molecules to the sample to compete with the target peptide ligand molecules and bind to the receptor molecules in place of the target peptide ligand molecules, releasing the target peptide ligand molecules; and
   separating and eluting the released target peptide ligand molecules from the remaining receptor molecules bound to labeled ligand molecules based on the presence or absence of a label on the ligands in the sample solution using a combination of surface-free isolation, specific competition elution and dual epitope isolation.

2. The method of claim 1 in which the labeled ligand molecules are labeled through hydrophilicity.

3. The method of claim 2 in which the target ligand molecules are separated from the labeled ligand molecules using a hydrophobic trap.

4. The method of claim 3 in which the hydrophobic trap uses reversed phase media to bind target peptides.

5. The method of claim 1 in which the labeled ligand molecules are labeled through fluorous compounds.

6. The method of claim 5 in which the fluorous compounds are ultra-hydrophobic.

7. The method of claim 5 in which the target ligand molecules are separated from the labeled ligand molecules using a hydrophobic trap.

8. The method of claim 5 in which the labeled molecules are eluted using an organic compound chosen from the group consisting of organic elutants more hydrophobic than the compound used to elute the target molecules and fluorous elutants more hydrophobic than the compound used to elute the target molecules.

9. The method of claim 7 in which the hydrophobic trap uses reversed phase media to bind target peptides.

10. The method of claim 1 where the labeled ligand molecules are peptides.

11. The method of claim 10 in which the target peptide ligand molecules are separated from the labeled ligand molecules using a hydrophobic trap.

12. The method of claim 11 in which the hydrophobic trap uses reversed phase media to bind target peptides.

13. The method of claim 1 where the target peptide ligand molecules are peptides, where the labeled ligand molecules and the target ligand molecules share the receptor epitope and the labeled ligand molecules consist of the receptor epitope plus amino acids that serve as labels.

14. The method of claim 1 where adding excess amounts of labeled ligand molecules to the sample to compete with the target peptide ligand molecules for binding to the receptor molecules whereby the receptor molecules release the target ligand molecules in favor of binding the labeled ligand molecules is performed in a diafiltration column.

15. The method of claim 1 in which the labeled ligand molecules employ peptides with amino acid sequences specific to the epitope of the target ligand molecules and unique amino acid sequences that serve as labels to competitively drive off the bound target peptides.

16. The method of claim 1 in which the method is carried out in a solvent at physiological conditions.

17. The method of claim 1 in which the target peptide ligand molecules are low-abundance proteins present in a plasma proteome.

18. A method of eluting target peptide ligand molecules bound to receptor molecules comprising:
   providing a sample solution containing target peptide ligand molecules bound to receptor molecules in the absence of immobilizing surfaces, where the receptor molecules are substantially larger than the target peptide ligand molecules;
   adding excess amounts of hydrophobic labeled ligand molecules to the sample to compete with the target peptide ligand molecules and bind to the receptor molecules in place of the target peptide ligand molecules, releasing the target peptide ligand molecules; and
   separating and eluting the released target peptide ligand molecules from the remaining receptor molecules bound to labeled ligand molecules based on the presence or absence of a hydrophobic label on the ligands in the sample solution using a combination of surface-free isolation, specific competition elution and dual epitope isolation.

19. A method of eluting target peptide ligand molecules bound to receptor molecules comprising:
   providing a sample solution containing target peptide ligand molecules bound to receptor molecules free in solution and in the absence of immobilizing surfaces, where the receptor molecules are substantially larger than the target peptide ligand molecules;
   adding excess amounts of fluorous labeled ligand molecules to the sample to compete with the target peptide ligand molecules and bind to the receptor molecules in place of the target ligand molecules, releasing the peptide ligand molecules; and
   separating and eluting the released peptide ligand molecules from the remaining receptor molecules bound to labeled ligand molecules based on the presence or absence of a fluorous compound label on the ligands in the sample solution using a combination of surface-free isolation, specific competition elution and dual epitope isolation.

* * * * *